US012044667B2

(12) United States Patent
Suzuki et al.

(10) Patent No.: US 12,044,667 B2
(45) Date of Patent: Jul. 23, 2024

(54) INFORMATION PROCESSING APPARATUS, CONTROL METHOD, AND NON-TRANSITORY STORAGE MEDIUM

(71) Applicant: NEC Corporation, Tokyo (JP)

(72) Inventors: Ryota Suzuki, Tokyo (JP); Riki Eto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 712 days.

(21) Appl. No.: 17/262,955

(22) PCT Filed: Jul. 31, 2018

(86) PCT No.: PCT/JP2018/028565
§ 371 (c)(1),
(2) Date: Jan. 25, 2021

(87) PCT Pub. No.: WO2020/026327
PCT Pub. Date: Feb. 6, 2020

(65) Prior Publication Data
US 2021/0311009 A1    Oct. 7, 2021

(51) Int. Cl.
*G01N 33/00* (2006.01)
*G01N 1/24* (2006.01)

(52) U.S. Cl.
CPC ........... *G01N 33/0067* (2013.01); *G01N 1/24* (2013.01); *G01N 33/0009* (2013.01);
(Continued)

(58) Field of Classification Search
CPC ........... G01N 33/0067; G01N 33/0011; G01N 33/0027; G01N 1/24; G01N 33/0009; G01N 33/0031; G01N 33/0016
(Continued)

(56) References Cited

U.S. PATENT DOCUMENTS 8,732,528 B1 * 5/2014 Zhang ............... G06F 17/18
714/25
9,122,705 B1 * 9/2015 Ioffe ................. G06F 16/583
(Continued)

FOREIGN PATENT DOCUMENTS

CN       112418395      *  2/2021  ............. G01N 27/12
CN       112464999      *  3/2021  ............. G01N 33/00
(Continued)

OTHER PUBLICATIONS

Shuichi Setoÿ et al, Analysis of Transient Response Output of Semiconductor Gas Sensor, Electrical Discourse E, 125 No. 3, 2005 (Year: 2005).*
(Continued)

*Primary Examiner* — Stephanie E Bloss
*Assistant Examiner* — Kevin C Butler

(57) ABSTRACT

An information processing apparatus (2000) acquires time-series data (14) output by a sensor (10) and computes a plurality of feature constants $\theta_i$ and a contribution value $\xi_i$ representing contribution with respect to the time-series data (14) for each feature constant $\theta_i$. Thereafter, the information processing apparatus (2000) outputs information in which a set $\Theta$ of the feature constants $\theta_i$ and a set $\Xi$ of the contribution values $\xi_i$ are associated with each other as a feature value of a target gas. As the feature constant $\theta$, a velocity constant $\beta$ or a time constant $\tau$ that is a reciprocal of the velocity constant can be adopted.

16 Claims, 12 Drawing Sheets

(52) U.S. Cl.
CPC ..... *G01N 33/0011* (2013.01); *G01N 33/0016* (2013.01); *G01N 33/0027* (2013.01); *G01N 33/0031* (2013.01)

(58) Field of Classification Search
USPC ........................................................ 73/23.2
See application file for complete search history.

(56) References Cited

U.S. PATENT DOCUMENTS

| | | | | |
|---|---|---|---|---|
| 10,121,156 | B2 * | 11/2018 | Takahashi | G06Q 30/0201 |
| 10,127,694 | B2 * | 11/2018 | Vlassis | G06T 11/206 |
| 10,309,924 | B2 * | 6/2019 | Jayant | C12Q 1/6869 |
| 10,909,457 | B2 * | 2/2021 | Tan | G06N 3/04 |
| 11,216,534 | B2 * | 1/2022 | Takada | G06F 17/18 |
| 11,468,364 | B2 * | 10/2022 | Shi | G06N 20/20 |
| 11,513,107 | B2 * | 11/2022 | Eto | G01N 33/0027 |
| 2009/0169089 | A1 * | 7/2009 | Hunt | G06F 18/24323 382/133 |
| 2012/0072141 | A1 * | 3/2012 | Hidai | G01R 21/001 702/60 |
| 2015/0339680 | A1 * | 11/2015 | Takahashi | G06Q 10/06 705/7.29 |
| 2016/0084808 | A1 * | 3/2016 | Bertholon | G01N 30/8693 73/23.35 |
| 2019/0012297 | A1 * | 1/2019 | Kobayashi | G06F 17/16 |
| 2019/0180194 | A1 * | 6/2019 | Kobayashi | G06N 3/0418 |
| 2020/0075134 | A1 * | 3/2020 | Shiba | G06N 20/00 |
| 2021/0224664 | A1 * | 7/2021 | Kisamori | G06F 30/27 |
| 2021/0232957 | A1 * | 7/2021 | Kisamori | G06N 20/10 |
| 2021/0248847 | A1 * | 8/2021 | Ito | G06N 5/02 |
| 2021/0293681 | A1 * | 9/2021 | Suzuki | G01N 5/02 |
| 2021/0311009 | A1 * | 10/2021 | Suzuki | G01N 33/0027 |
| 2022/0018823 | A1 * | 1/2022 | Eto | G01N 19/00 |
| 2022/0036223 | A1 * | 2/2022 | Eto | G06N 7/00 |
| 2022/0172086 | A1 * | 6/2022 | Katz | G06N 7/01 |
| 2022/0221839 | A1 * | 7/2022 | Eto | G05B 19/416 |
| 2022/0309397 | A1 * | 9/2022 | Yamada | G06N 20/00 |

FOREIGN PATENT DOCUMENTS

| | | | | |
|---|---|---|---|---|
| EP | 4148623 | A1 * | 3/2023 | ............ G06N 3/0985 |
| FR | 3026188 | A1 * | 3/2016 | ............ G01N 30/64 |
| JP | 2845554 | B2 * | 12/1991 | ............ G01N 21/17 |
| JP | H03-276046 | A | 12/1991 | |
| JP | H11-264809 | A | 9/1999 | |
| JP | H11264809 | A * | 9/1999 | ............ G01N 27/12 |
| JP | 3815041 | B2 * | 8/2006 | |
| JP | 2006-275606 | A | 10/2006 | |
| JP | 2006275606 | A * | 10/2006 | |
| JP | 2012064023 | A * | 3/2012 | ......... G01R 19/2516 |
| JP | 5598200 | B2 * | 10/2014 | ......... G01R 19/2516 |
| JP | 2014-221005 | A | 11/2014 | |
| JP | 2017-156254 | A | 9/2017 | |
| JP | 2018506722 | A * | 6/2018 | ............ G06F 17/30 |
| JP | 2019016193 | A * | 1/2019 | ............ G06F 17/16 |
| JP | 6663151 | B2 * | 3/2020 | ............ G01N 19/00 |
| JP | 7099623 | B2 * | 7/2022 | ......... G01N 33/0073 |
| WO | 2004/090517 | A1 | 10/2004 | |
| WO | WO-2004090517 | A1 * | 10/2004 | ......... G01N 21/6408 |
| WO | 2014/103560 | A1 | 7/2014 | |
| WO | WO-2014103560 | A1 * | 7/2014 | ............ G06Q 10/06 |
| WO | 2018/101128 | A1 | 6/2018 | |
| WO | WO-2018101128 | A1 * | 6/2018 | ............ G01N 19/00 |
| WO | WO-2020026326 | A1 * | 2/2020 | ............ G01N 5/02 |
| WO | WO-2020026327 | A1 * | 2/2020 | ......... G01N 33/0011 |
| WO | WO-2020065806 | A1 * | 4/2020 | ......... G01N 33/0036 |
| WO | WO-2020100285 | A1 * | 5/2020 | ......... G01N 33/0027 |
| WO | WO-2020202338 | A1 * | 10/2020 | ......... G01N 33/0073 |
| WO | WO-2023037999 | A1 * | 3/2023 | |

OTHER PUBLICATIONS

By Ye Zhang et al., Estimating the Rate Constant From Biosensor Data via an Adaptive Variational Bayesian Approach, The Annals of Applied Statistics 2019, vol. 13, No. 4, 2011-2042 (Year: 2019).*
Ben Lambert et al., R*: A Robust MCMC Convergence Diagnostic with Uncertainty Using Decision Tree Classifiers, International Society for Bayesian Analysis, 2022, 17, No. 2, pp. 353-379 (Year: 2022).*
Tantithamthavorn et al., An Empirical Comparison of Model Validation Techniques for Defect Prediction Models, IEEE Transactions on Software Engineering, vol. 43, No. 1, Jan. 2017 (Year: 2017).*
Hébert et al., The Living Planet Index's ability to capture biodiversity change from uncertain data, Ecological Society of America, Mar. 21, 2023, pp. 1-13 (Year: 2023).*
Wu et al., Bayesian Annealed Sequential Importance Sampling (BASIS): an unbiased version of Transitional Markov Chain Monte Carlo, American Society of Mechanical Engineers, https://doi.org/10.1115/1.4037450, 2018, p. 18 (Year: 2018).*
Roopnarine et al., The description and classification of evolutionary mode: A computational approach, The Paleontological Society., 2001, 27(3), 2001, pp. 446-465 (Year: 2001).*
International Search Report for PCT Application No. PCT/JP2018/028565, mailed on Oct. 9, 2018.
Shuichi Seto et al., Chemical Analysis for Transient Response of Semiconductor Sensor by Autoregressive Model. IEEJ Transactions on Sensors and Micromachines., 2005, Japan, vol. 125, No. 3, pp. 129-134.
Japanese Office Action for JP Application No. 2020-533925 mailed on Jan. 18, 2022 with English Translation.
Kensuke Sekihara, "Bayesian signal processing", 1st edition, 2nd printing, Jan. 10, 2016, pp. 9-32, Kyoritsu Shuppan Co., Ltd., Japan.

* cited by examiner

FIG. 8
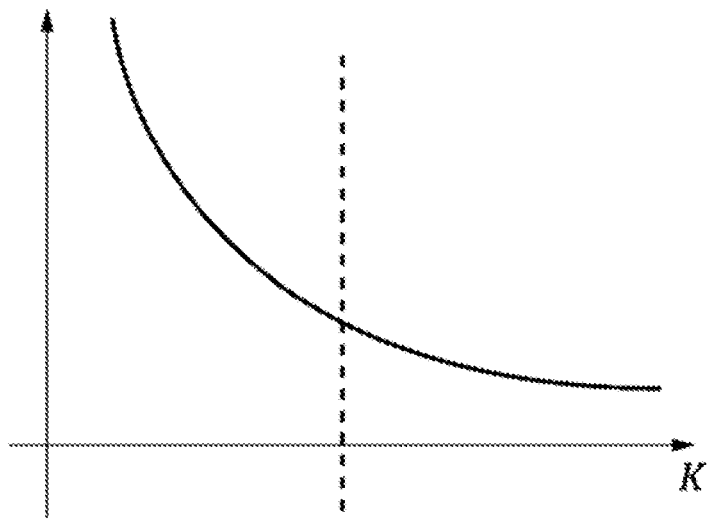
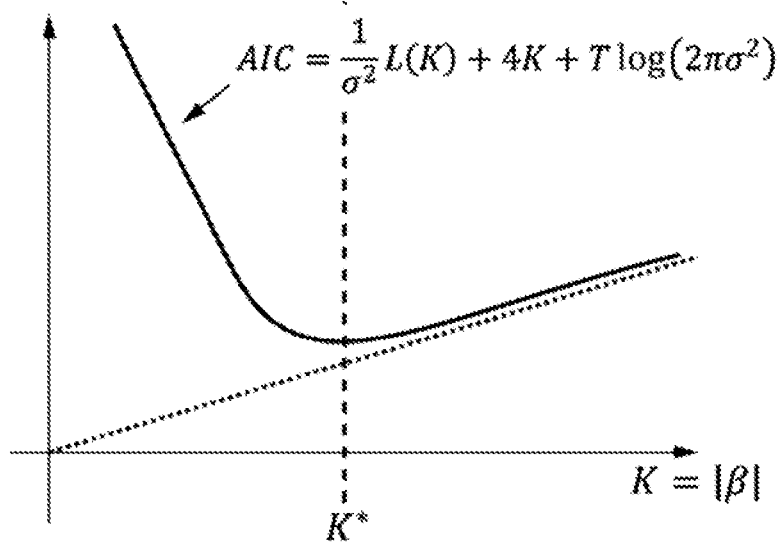

ically, since a diffusion time
INFORMATION PROCESSING APPARATUS, CONTROL METHOD, AND NON-TRANSITORY STORAGE MEDIUM This application is a National Stage Entry of PCT/JP2018/028565 filed on Jul. 31, 2018, the contents of all of which are incorporated herein by reference, in their entirety.

TECHNICAL FIELD

The present invention relates to an analysis of a feature of gas.

BACKGROUND ART

A technique has been developed to obtain information related to gas by measuring the gas with a sensor. Patent Document 1 discloses a technique for discriminating the type of sample gas by using a signal (time-series data of detected values) obtained by measuring the sample gas with a nanomechanical sensor. Specifically, since a diffusion time constant of the sample gas with respect to a receptor of the sensor is determined by a combination of the type of the receptor and the type of the sample gas, it is disclosed that the type of the sample gas can be discriminated based on the diffusion time constant obtained from the signal and the type of the receptor.

RELATED DOCUMENT

Patent Document

[Patent Document 1] Japanese Patent Application Publication No. 2017-156254

SUMMARY OF THE INVENTION

Technical Problem

In Patent Document 1, it is assumed that one type of molecule is contained in the sample gas, and it is not assumed that the sample gas in which a plurality of types of molecules are mixed is handled. The present invention has been made in view of the above problems and is to provide a technique for extracting a feature of gas in which a plurality of types of molecules are mixed.

Solution to Problem

An information processing apparatus of the present invention includes: 1) a time-series data acquisition unit that acquires time-series data of detected values output from a sensor where a detected value thereof changes according to attachment and detachment of a molecule contained in a target gas; 2) a computation unit that computes a plurality of feature constants contributing with respect to the time-series data and a contribution value representing a magnitude of contribution for each feature constant with respect to the time-series data; and 3) an output unit that outputs a combination of the plurality of feature constants and the contribution values computed for each feature constant as a feature value of gas sensed by the sensor. The feature constant is a time constant or a velocity constant related to a magnitude of a temporal change of the number of molecules attached to the sensor.

A control method of the present invention is executed by a computer. The control method includes: 1) a time-series data acquisition step of acquiring time-series data of detected values output from a sensor where a detected value thereof changes according to attachment and detachment of a molecule contained in a target gas; 2) a computation step of computing a plurality of feature constants contributing with respect to the time-series data and a contribution value representing a magnitude of contribution for each feature constant with respect to the time-series data; and 3) an output step of outputting a combination of the plurality of feature constants and the contribution values computed for each feature constant as a feature value of gas sensed by the sensor. The feature constant is a time constant or a velocity constant related to a magnitude of a temporal change of the number of molecules attached to the sensor.

A program of the present invention causes a computer to execute each step included in the control method of the present invention.

Advantageous Effects of Invention

According to the present invention, there is provided a technique for extracting a feature of gas in which a plurality of types of molecules are mixed.

BRIEF DESCRIPTION OF THE DRAWINGS

The above-described object, other objects, features, and advantages will be further clarified by the preferred embodiments described below and the accompanying drawings.

FIG. 8 is a diagram representing AIC with a graph.

DESCRIPTION OF EMBODIMENTS

Hereinafter, embodiments of the present invention will be described with reference to the drawings. In all the drawings, the same constituents will be referred to with the same numerals, and the description thereof will not be repeated. Further, in each block diagram, each block represents a functional unit configuration, not a hardware unit configuration, unless otherwise specified.

Example Embodiment 1

<Outline of Invention and Theoretical Background>

Figure 1:
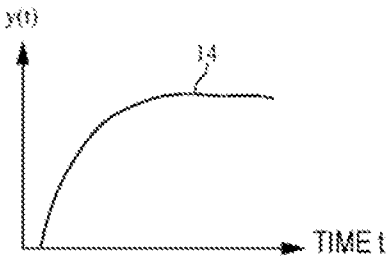
FIG. 1 is a diagram illustrating an outline of an information processing apparatus according to Example Embodiment 1.
Figure 2:
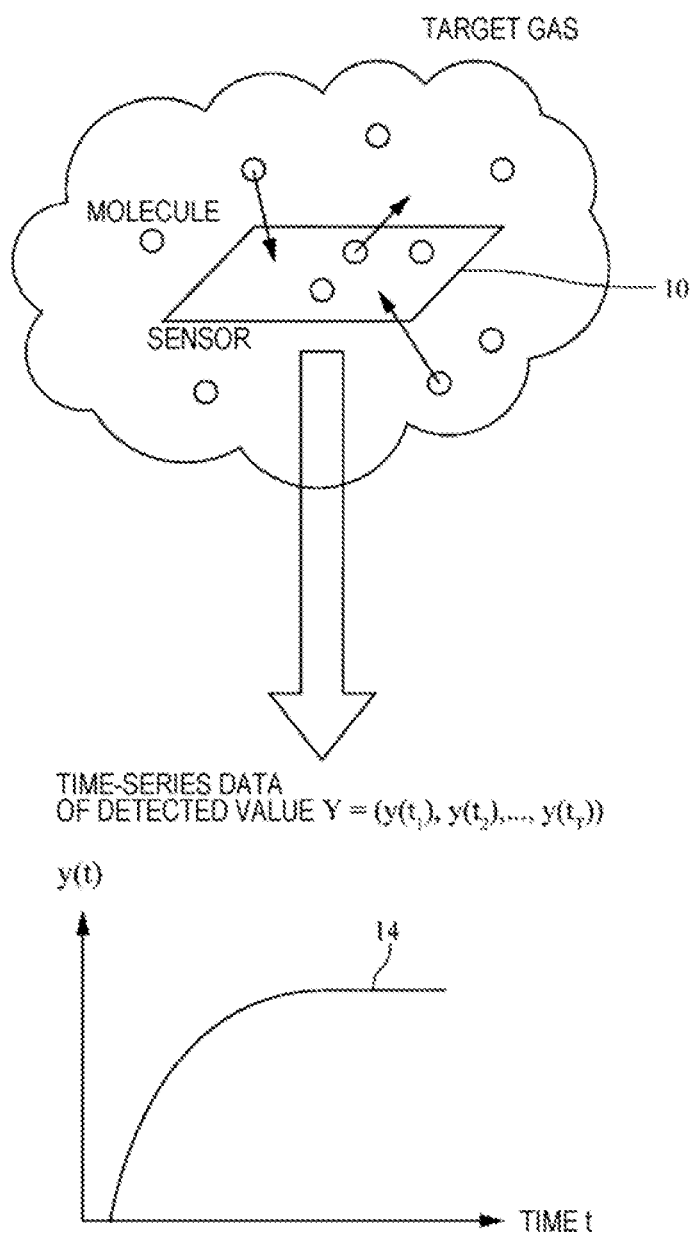
FIG. 2 is a diagram illustrating a sensor for obtaining data acquired by the information processing apparatus.

FIG. 1 is a diagram illustrating an outline of the information processing apparatus 2000 of Example Embodiment 1. Further, FIG. 2 is a diagram illustrating a sensor 10 for obtaining data acquired by the information processing apparatus 2000. The sensor 10 is a sensor that has a receptor to which a molecule is attached and whose detected value is changed according to attachment and detachment of the molecule at the receptor. Note that, the gas sensed by the sensor 10 is called a target gas. Further, time-series data of detected values output from the sensor 10 is called time-series data 14. When necessary, the time-series data 14 is also expressed as Y, and the detected value at time t is also expressed as y(t). Y is a vector in which y(t) is enumerated.

For example, the sensor 10 is a Membrane-type Surface Stress (MSS) sensor. The MSS sensor has a functional membrane to which a molecule is attached as a receptor, and stress generated in a supporting member of the functional membrane is changed due to the attachment and detachment of the molecule with respect to the functional membrane. The MSS sensor outputs the detected value based on the change in the stress. Note that, the sensor 10 is not limited to the MSS sensor, may output the detected value based on changes in physical quantities related to the viscoelasticity and dynamic characteristics (the mass, the moment of inertia, or the like) of a member of the sensor 10 that occur in response to the attachment and detachment of the molecule with respect to the receptor, and can adopt various types of sensors such as a cantilever type, a membrane type, an optical type, a Piezo, and an oscillation response.

For the sake of explanation, sensing by the sensor 10 is modeled as follows.

(1) The sensor 10 is exposed to the target gas containing K types of molecules.
(2) The concentration of each molecule k in the target gas is a constant ρk.
(3) A total of N molecules can be adsorbed on the sensor 10.
(4) At time t, the number of molecules k attached to the sensor 10 is nk(t).

The temporal change of the number of molecules k nk(t) attached to the sensor 10 can be formulated as follows.

$$\frac{dn_k(t)}{dt} = \alpha_k \rho_k - \beta_k n_k(t) \quad (1)$$

The first and second terms on the right side in Expression (1) represent the amount of increase (the number of molecules k newly attached to the sensor 10) and the amount of decrease (the number of molecules k detached from sensor 10) of the molecules k per unit time, respectively. Further, αk is a velocity constant representing a velocity at which the molecule k is attached to the sensor 10, and βk is a velocity constant representing a velocity at which the molecule k is detached the sensor 10.

Since the concentration ρk is constant, the number of molecules k nk(t) at time t can be formulated from the above Expression (1) as follows.

$$n_k(t) = n_k^* + (n_k(t_0) - n_k^*)e^{-\beta_k t} \text{ wherein } n_k^* := \frac{\beta_k \rho_k}{\alpha_k} \quad (2)$$

Further, assuming that no molecule is attached to the sensor 10 at time t0 (initial state), nk(t) is represented as follows.

$$n_k(t) = n^*_k(1 - e^{-\beta_k t}) \quad (3)$$

The detected value of the sensor 10 is determined by the stress acting on the sensor 10 by the molecules contained in the target gas. It is considered that the stress acting on the sensor 10 by a plurality of molecules can be represented by the linear sum of the stress acting on individual molecules. However, the stress generated by the molecule is considered to differ depending on the type of molecule. That is, it can be said that the contribution of the molecule with respect to the detected value of the sensor 10 differs depending on the type of the molecule.

Thereby, the detected value y(t) of the sensor 10 can be formulated as follows.

$$y(t) = \sum_{k=1}^{K} \gamma_k n_k(t) \quad (4)$$

$$= \begin{cases} \xi_0 - \sum_{k=1}^{K} \xi_k e^{-\beta_k t} & \text{when rising} \\ \sum_{k=1}^{K} \xi_k e^{-\beta_k t} & \text{when falling} \end{cases}$$

$$\text{wherein } \xi_k = \frac{\gamma_k \alpha_k \rho_k}{\beta_k} \ (k = 1, \dots, K), \xi_0 = \sum_{k=1}^{K} \xi_k$$

Both γk and ξk represent the contribution of the molecule k with respect to the detected value of the sensor 10. Note that, the meanings of "rising" and "falling" will be described later. When the time-series data 14 obtained from the sensor 10 that senses the target gas can be decomposed as in the above Expression (4), it is possible to recognize the types of molecules contained in the target gas and the ratio of each type of molecules contained in the target gas. That is, by the decomposition represented by Expression (4), data representing the feature of the target gas (that is, the feature value of the target gas) can be obtained.

The information processing apparatus 2000 acquires the time-series data 14 output by the sensor 10 and decomposes the time-series data 14 as shown in the following Expression (5).

$$y(t) = \sum_{i=1}^{m} \xi_i f(\sigma_i) \quad (5)$$

$\xi_i$ is a contribution value representing the contribution of the feature constant $\theta_i$ with respect to the detected value of the sensor 10.

Specifically, first, by using the time-series data 14, the information processing apparatus 2000 computes a set of the plurality of feature constants $\Theta = \{\theta_1, \dots, \theta_m\}$ that contribute with respect to the time-series data 14, and a contribution value $\xi_i$ that represents the magnitude of the contribution of each feature constant $\theta_i$ with respect to the time-series data 14. Note that, as will be described later, there are cases where the contribution value $\xi_i$ is computed after the feature constant $\theta_i$ is computed, and cases where the contribution value $\xi_i$ is computed together with the feature constant $\theta_i$.

Further, the information processing apparatus 2000 outputs information in which the set Θ of the feature constants and the set Ξ of the contribution values are associated with each other as a feature value representing the feature of the target gas. The association between the set Θ of the feature constants and the set Ξ of contribution values is represented by, for example, a feature matrix F with m rows and 2 columns (m is the number of feature constants and the number of contribution values). For example, this matrix F has a feature constant vector Θ=(θ$_1$, . . . , θ$_m$) representing a set of the feature constants in a first column, and also has a contribution vector Ξ=(ξ$_1$, . . . , ξ$_m$) representing a set of contribution values in a second column.

That is, F=(ΘT, ΞT). In the following description, unless otherwise specified, the feature value of the target gas is represented by the feature matrix F. However, the feature value of the target gas does not necessarily have to be represented as a vector.

As the feature constant θ, the above-mentioned velocity constant β or the time constant T, which is the reciprocal of the velocity constant, can be adopted. Expression (5) can be represented as follows for each of the cases where β and τ are used as θ.

$$y(t) = \sum_{i=1}^{m} \xi_i e^{-\beta_i t} \quad (6)$$

$$y(t) = \sum_{i=1}^{m} \xi_i e^{-t/\tau_i} \quad (7)$$

Note that, in FIG. 1, the velocity constant β is used as the feature constant. Therefore, the set Θ of feature constants shows β$_1$ to β$_m$.

<Action and Effect>

As described above, since the contribution of the molecule with respect to the detected value of the sensor 10 is considered to differ depending on the type of the molecule, the above-mentioned set Θ of the feature constants and the set Ξ of the contribution values, which corresponds to the set Θ of the feature constants, are considered to be different depending on the type of the molecule contained in the target gas and a mixing ratio thereof. Therefore, the information, in which the set Θ of the feature constants and the set Ξ of the contribution values are associated with each other, can be used as information that can distinguish gas in which a plurality of types of molecules are mixed, from each other, that is, as the feature value of the gas.

Therefore, the information processing apparatus 2000 of the present example embodiment computes the set Θ of the feature constants and the set Ξ of the contribution values that represents the contribution of each feature constant with respect to the time-series data 14 based on the time-series data 14 obtained by sensing the target gas with the sensor 10 and outputs the information in which the computed sets Θ and Ξ are associated with each other as the feature value of the target gas. By doing so, the feature value capable of identifying the gas in which the plurality of types of molecules are mixed can be automatically generated from the result of sensing the gas with the sensor 10.

Note that, the above description with reference to FIG. 1 is an example for facilitating understanding of the information processing apparatus 2000 and does not limit the function of the information processing apparatus 2000. Hereinafter, the information processing apparatus 2000 of the present example embodiment will be described in more detail.

<Example of Functional Configuration of Information Processing Apparatus 2000>

Figure 3:
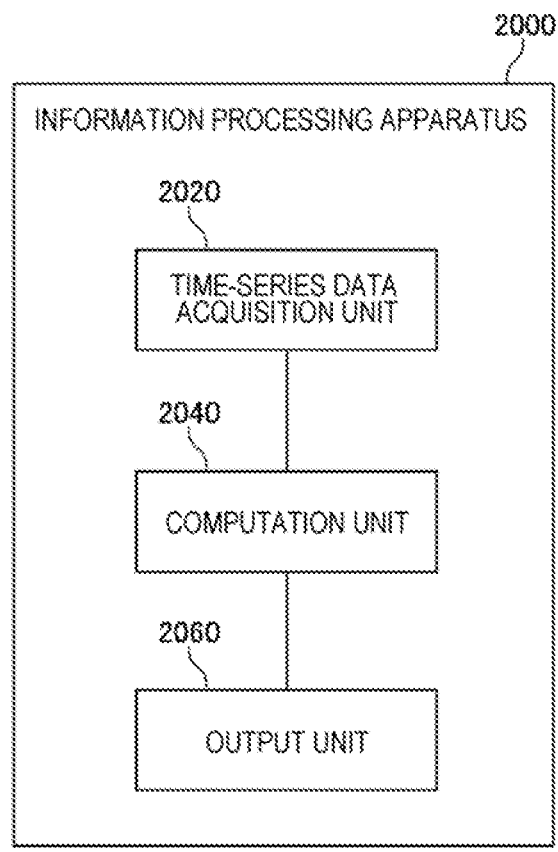
FIG. 3 is a diagram illustrating a functional configuration of the information processing apparatus according to Example Embodiment 1.

FIG. 3 is a diagram illustrating a functional configuration of the information processing apparatus 2000 according to Example Embodiment 1. The information processing apparatus 2000 includes a time-series data acquisition unit 2020, a computation unit 2040, and an output unit 2060. The time-series data acquisition unit 2020 acquires the time-series data 14 from the sensor 10. The feature constant generation unit 2030 computes the plurality of feature constants θ$_i$ and the contribution value ξ$_i$ that represents the magnitude of the contribution of each feature constant θ$_i$ with respect to the time-series data 14, by using the time-series data 14. The output unit 2060 outputs the information in which the set Θ of the feature constants and the set Ξ of the contribution values are associated with each other as the feature value of the gas sensed by the sensor 10.

<Hardware Configuration of Information Processing Apparatus 2000>

Each functional configuration unit of the information processing apparatus 2000 may be implemented by hardware (for example, a hard-wired electronic circuit or the like) that implements each functional configuration unit, or may be implemented by a combination of hardware and software (for example, a combination of an electronic circuit and a program for controlling the electronic circuit). Hereinafter, a case where each functional configuration unit of the information processing apparatus 2000 is implemented by a combination of hardware and software will be further described.

Figure 4:
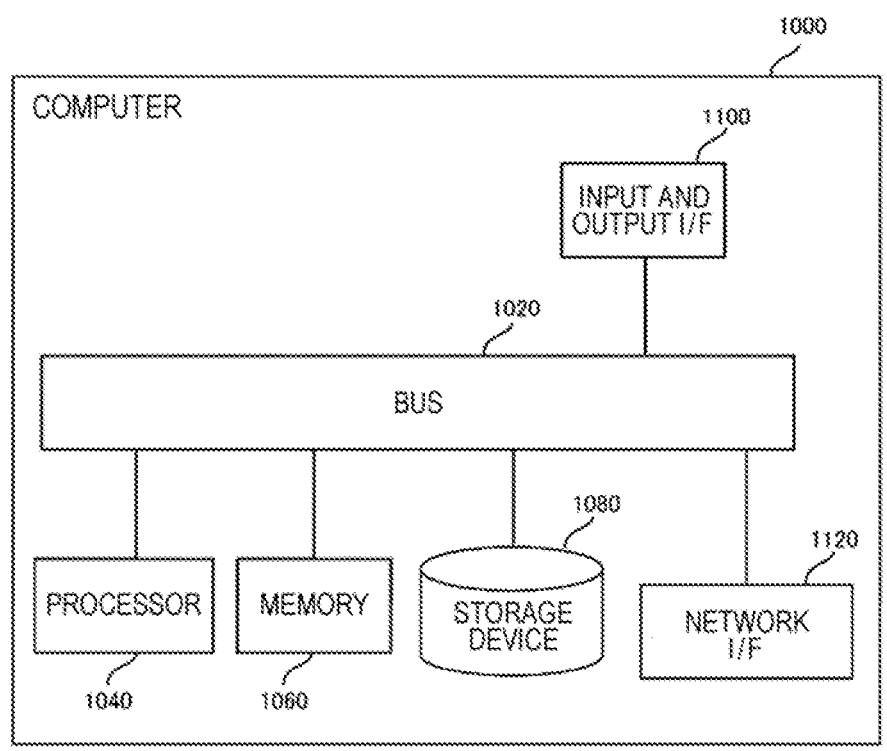
FIG. 4 is a diagram illustrating a computer for implementing the information processing apparatus.

FIG. 4 is a diagram illustrating a computer 1000 for implementing the information processing apparatus 2000. The computer 1000 is any computer. For example, the computer 1000 is a stationary computer such as a personal computer (PC) or a server machine. In addition, for example, the computer 1000 is a portable computer such as a smartphone or a tablet terminal. The computer 1000 may be a dedicated computer designed to implement the information processing apparatus 2000 or may be a general-purpose computer.

The computer 1000 includes a bus 1020, a processor 1040, a memory 1060, a storage device 1080, an input and output interface 1100, and a network interface 1120. The bus 1020 is a data transmission path for the processor 1040, the memory 1060, the storage device 1080, the input and output interface 1100, and the network interface 1120 to mutually transmit and receive data. However, the method of connecting the processors 1040 and the like to each other is not limited to the bus connection.

The processor 1040 is various processors such as a Central Processing Unit (CPU), a Graphics Processing Unit (GPU), and a Field-Programmable Gate Array (FPGA). The memory 1060 is a main storage device implemented by using a Random Access Memory (RAM) or the like. The storage device 1080 is an auxiliary storage device implemented by using a hard disk, a Solid State Drive (SSD), a memory card, a Read Only Memory (ROM), or the like.

The input and output interface 1100 is an interface for connecting the computer 1000 and the input and output devices. For example, an input device such as a keyboard or an output device such as a display device is connected to the input and output interface 1100. In addition, for example, the sensor 10 is connected to the input and output interface 1100. However, the sensor 10 does not necessarily have to be directly connected to the computer 1000. For example, the sensor 10 may store the time-series data 14 in a storage device shared with the computer 1000.

The network interface 1120 is an interface for connecting the computer 1000 to a communication network. The communication network is, for example, a Local Area Network (LAN) or a Wide Area Network (WAN). A method of connecting the network interface 1120 to the communication network may be a wireless connection or a wired connection.

The storage device 1080 stores a program module that implements each functional configuration unit of the information processing apparatus 2000. The processor 1040 implements the function corresponding to each program module by reading each of these program modules into the memory 1060 and executing the modules.

<Process Flow>

Figure 5:
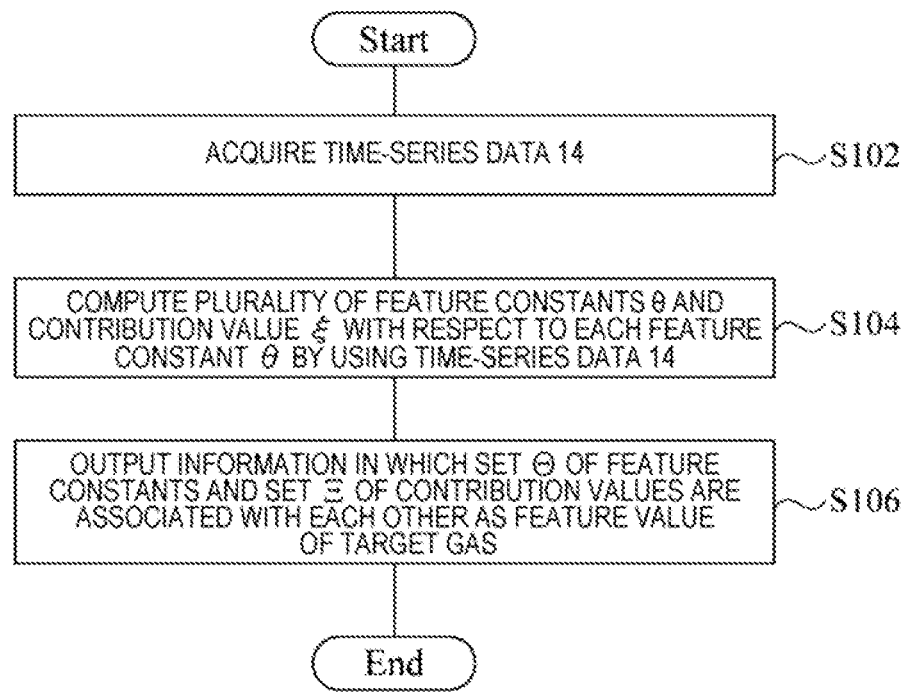
FIG. 5 is a flowchart illustrating a flow of a process executed by the information processing apparatus of Example Embodiment 1.

FIG. 5 is a flowchart illustrating a flow of a process executed by the information processing apparatus 2000 of Example Embodiment 1. The time-series data acquisition unit 2020 acquires the time-series data 14 (S102). The computation unit 2040 computes the plurality of feature constants $\theta_i$ and the contribution value $\xi_i$ corresponding to each feature constant $\theta_i$ by using the time-series data 14 (S104). The output unit 2060 outputs the information in which the set of the feature constants and the set of the contribution values are associated with each other as the feature value of the target gas (S106).

The timing at which the information processing apparatus 2000 executes the series of processes illustrated in FIG. 5 varies. For example, the information processing apparatus 2000 receives an input operation for specifying the time-series data 14 and executes the series of processes for the specified time-series data 14. In addition, for example, the information processing apparatus 2000 waits such that the time-series data 14 can be received and executes the processes after S104 according to the reception of the time-series data 14 (that is, the execution of S102).

<Acquisition of Time-Series Data 14: S102>

The time-series data acquisition unit 2020 acquires the time-series data 14 (S102). A method is any method in which the time-series data acquisition unit 2020 acquires the time-series data 14. For example, the information processing apparatus 2000 acquires the time-series data 14 by accessing a storage device in which the time-series data 14 is stored. The storage device in which the time-series data 14 is stored may be provided inside the sensor 10 or may be provided outside the sensor 10. In addition, for example, the time-series data acquisition unit 2020 may acquire the time-series data 14 by sequentially receiving the detected values output from the sensor 10.

The time-series data 14 is time-series data in which the detected values output by the sensor 10 are arranged in the order of earliest time output from the sensor 10. However, the time-series data 14 may be obtained by adding predetermined preprocessing with respect to the time-series data of the detected values obtained from the sensor 10. Further, instead of acquiring the preprocessed time-series data 14, the time-series data acquisition unit 2020 may perform preprocessing with respect to the time-series data 14. As the preprocessing, for example, filtering for removing noise components from time-series data can be adopted.

The time-series data 14 is obtained by exposing the sensor 10 to the target gas. However, when performing a measurement related to the gas using the sensor, by repeating an operation of exposing the sensor to the gas to be measured and an operation of removing the gas to be measured from the sensor, a plurality of time-series data to be analyzed may be obtained from the sensor.

Figure 6:
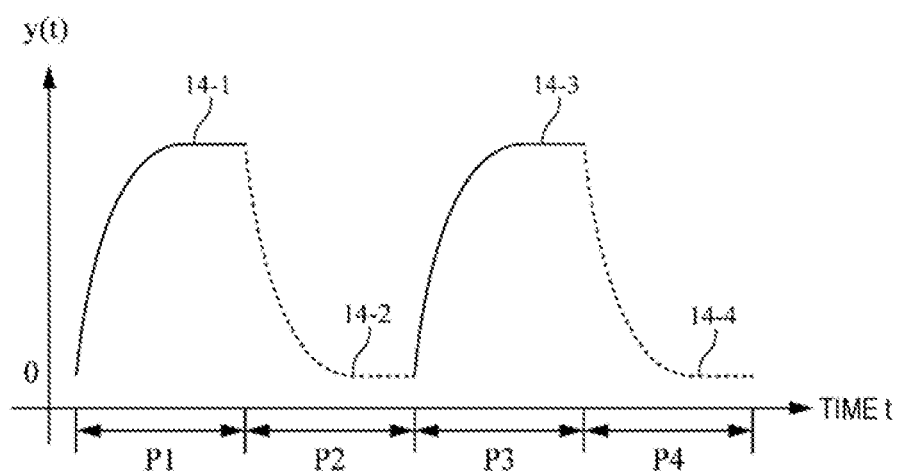
FIG. 6 is a diagram illustrating a plurality of time-series data obtained from the sensor.

FIG. 6 is a diagram illustrating a plurality of time-series data obtained from the sensor. In FIG. 6, the rising time-series data is represented by a solid line, and the falling time-series data is represented by a dotted line so that the rising time-series data and the falling time-series data can be easily distinguished. In FIG. 6, the time-series data 14-1 of a period P1 and the time-series data 14-3 of a period P3 are obtained by the operation of exposing the sensor to the gas to be measured. When the sensor is exposed to the gas to be measured in this way, the detected value of the sensor increases. The time-series data obtained by exposing the sensor to the gas to be measured in this way is also called "rising" time-series data. The "when rising" in Expression (4) means "in a case where the time-series data 14 is rising time-series data". The same applies to the following expressions.

On the other hand, the time-series data 14-2 of a period P2 and the time-series data 14-4 of a period P4 are obtained by the operation of removing the gas to be measured from the sensor. Note that, the operation of removing the gas to be measured from the sensor is implemented, for example, by exposing the sensor to gas called purge gas. When the operation of removing the gas to be measured from the sensor is performed in this way, the detected value of the sensor decreases. The time-series data obtained by the operation of removing the gas to be measured from the sensor is also called "falling" time-series data. The "when falling" in Expression (4) means "in a case where the time-series data 14 is falling time-series data". The same applies to the following expressions.

In the information processing apparatus 2000, the time-series data 14 obtained by each of the operations of exposing the sensor 10 to the target gas and the operation of removing the target gas from the sensor 10 are distinguished and are treated as different time-series data 14. For example, in the example in FIG. 6, the time-series data obtained in each of the four periods P1 to P4 are treated as different time-series data 14. Therefore, when a series of time-series data is obtained by repeating the operation of exposing the sensor 10 to the target gas and the operation of removing the target gas from the sensor 10, it is necessary to divide the series of time-series data into a plurality of time-series data 14.

Various methods can be adopted as a method for obtaining the plurality of time-series data 14 by dividing the series of time-series data obtained from the sensor 10. For example, the plurality of time-series data 14 can be obtained by manually dividing the series of time-series data obtained from the sensor 10. In addition, for example, the information processing apparatus 2000 may acquire the series of time-series data and obtain the plurality of time-series data 14 by dividing the time-series data.

Note that, various methods can be adopted as the method of dividing the time-series data by the information processing apparatus 2000. For example, there are the following methods.

<<(a) Method Using First Derivative>>

In the time-series data 14, the derivative of a sensor value becomes discontinuous at a portion to be divided, and the absolute value becomes maximum immediately after that. Therefore, the time-series data 14 can be divided by using a point where the absolute value of the first derivative becomes large.

<<(b) Method Using Second Derivative>>

Similarly, the derivative is discontinuous at the point to be divided, so the second derivative diverges to infinity. Therefore, the time-series data 14 can be divided by using a point where the absolute value of the second derivative becomes large.

<<(c) Method of Using Metadata Obtained from Sensor>>

Depending on the type of sensor, metadata other than the detected value is provided. For example, in the MSS module, different pumps (sample pump and purge pump) are prepared for suction of the gas (sample) to be measured and the purge gas and by turning these pumps on and off alternately, the measurement of rising and the measurement of falling are performed. Further, an operation sequence of the pump (information representing which pump is used for the detected value, the flow rate measurement value used for the feedback control of the flow rate, or the like) is added to the recorded detected value as time-series information. Therefore, for example, the information processing apparatus 2000 can divide the time-series data 14 by using the operation sequence of the pump obtained together with the time-series data 14.

<<Combination of the Above Methods>>

Regarding the method (c), it is preferable to make a correction in consideration of the delay from the operation of the pump to the arrival of the gas at the sensor. Therefore, for example, the information processing apparatus 2000 tentatively divides the time-series data 14 into a plurality of sections by using the method (c) and then determines a time point at which the absolute value of the first derivative becomes maximum in each section, and divides the time-series data 14 at each determined time point.

Note that, the information processing apparatus 2000 may be configured to use only one of the time-series data 14 obtained by the operation of exposing the sensor 10 to the target gas and the time-series data 14 obtained by the operation of removing the target gas from the sensor 10.

<Computation of Feature Constant and Contribution Value: S104>

The computation unit 2040 computes the plurality of feature constants $\theta_i$ and the contribution value $\xi_i$ corresponding to the feature constant $\theta_i$ by using the time-series data 14 (S104). This process corresponds to decomposing the time-series data 14 into the sum of $\xi_i * f(\theta_i)$ shown in Expression (5).

Various methods can be used for the method in which the computation unit 2040 computes the feature constant and the contribution value thereof from the time-series data 14. Hereinafter, the method of computing the feature constant will be described first. Note that, in some cases, the contribution value is computed in the process of computing the feature constant. This case will be described later.

<<Computation Method 1 of Feature Constant>>

For example, the computation unit 2040 computes the set of the feature constants based on a slope of log [y'(t)] obtained by taking log as the derivative y'(t) of the time-series data 14. log [y'(t)] is expressed as follows.

$$g(t) = \log[y'(t)] \quad (8)$$
$$= \log\left[\frac{d\{\sum_{i=1}^{m} \xi_i e^{-\beta_i t}\}}{dt}\right]$$
$$= \log\sum_{i=1}^{m} \exp(C_i - \beta_i t)$$

wherein, $C_i = \ln(-\beta_i \xi_i)$

Note that, since a log is taken, it is assumed that y'(t) is always positive. In the case where y'(t) is negative, the feature constant is computed by using another method described later.

Figure 7:
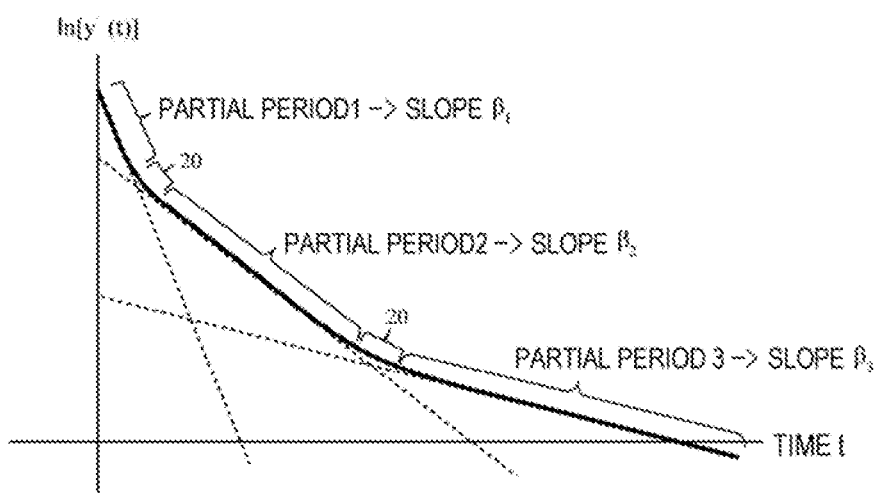
FIG. 7 is a diagram illustrating a graph of g(t).

FIG. 7 is a diagram illustrating a graph of g(t). By Expression (8), it is known that g(t)=log [y'(t)] is a function having a form of the so-called log-sum-exp, and this function takes a value close to the maximum value of the accumulated exp. That is, in Expression (8), the value of g(t) is close to the maximum value of $c_i - \beta_i t$ at the time t.

When $g(t) = c_i - \beta_i t$ is approximately set, the slope g'(t) of this function becomes the velocity constant $\beta_i$. Therefore, the slope g'(t) of g(t) at time t is substantially the same as $\beta_i$ corresponding to i at which $c_i - \beta_i t$ is maximum at the time. Further, since $\exp(c_i - \beta_i t)$ is a monotonically decreasing function, it can be said that the slope of g(t) changes stepwise as illustrated in FIG. 7.

Therefore, the computation unit 2040 computes the slope g'(t) of g(t) at each time t and extracts a plurality of periods (hereafter, a partial period) in which g'(t) is substantially the same from a domain (a measurement period of time-series data 14) of g(t). The computation unit 2040 computes g'(t) in each extracted partial period as the velocity constant $\beta_i$. For example, the computation unit 2040 computes a statistical value (average value or the like) of g'(t) in each partial period as the velocity constant corresponding to the partial period. In addition, for example, the computation unit 2040 may perform linear regression on (t, g(t)) included in the partial period for each partial period and may use the slope of the regression line obtained for each partial period as the velocity constant. Note that, the period during which g'(t) is substantially the same can be determined, for example, by clustering a set of g'(t) based on the magnitude of the value thereof.

For example, in FIG. 7, three partial periods are extracted from the domain of g(t). The computation unit 2040 computes $\beta_1$, $\beta_2$, and $\beta_3$ as the velocity constants corresponding to each of these three partial periods. In this way, the set of the feature constants $\Theta = \{\beta_1, \beta_2, \beta_3\}$ is computed.

As in the section 20 illustrated in FIG. 7, a slope different from any of the slopes before and after the slope may appear in a portion where the slope of g(t) is changed for a short period of time. The slope that appears only for such a short period may not be included in the feature constants.

For example, the minimum value of a length of the partial period is predetermined. The computation unit 2040 divides the domain of g(t) into a plurality of periods based on the magnitude of the slope g'(t) and extracts only the period having a length equal to or greater than the minimum value as the above-mentioned partial period (that is, g'(t) corresponding to a period having a length less than the minimum value is not included in the set of the feature constants). By doing so, g'(t) that appears only for a short period of time can be excluded from the feature constants. Note that, the minimum value of the length of the partial period can also be represented as the minimum value of the number of detected values included in the partial period.

In addition, for example, the computation unit 2040 may determine the number of feature constants m by using a method described later and extract as many partial periods as that number from the domain of g(t). In this case, for example, the computation unit 2040 divides the domain of g(t) into the plurality of periods based on the magnitude of the slope g'(t) and extracts m periods, which are higher in terms of the length of the period, as the above-mentioned partial periods.

<<Computation Method 2 of Feature Constant>>

In order to adopt the above-mentioned computation method 1, it is necessary to take the log of y'(t), so the value of y'(t) should always be positive. In contrast to this, in the computation method 2 described here, it can be used even when the value of y'(t) becomes negative while using the index corresponding to the slope g'(t) of g(t) described above.

First, g'(t), which is the slope of g(t)=log [y'(t)] described above, can be represented as follows.

$$g'(t) = \frac{d}{dt}[\log y'(t)] \qquad (9)$$
$$= \frac{y''(t)}{y'(t)}$$

In the computation method 2, by using y''(t)/y'(t) as the index corresponding to the slope g'(t) of g(t) without taking the log of y'(t), the case where y'(t) is negative can be also handled.

g'(t) can be said to be a direction of the vector (y'(t), y''(t)). In other words, g'(t) can be said to be a direction of the velocity vector (vector representing the temporal change) of the vector (y(t), y'(t)).

The computation unit 2040 computes the vector (y(t), y'(t)) for each time t, and uses each of the computed vectors to compute the velocity vector (y(t+1)−y (t), y'(t+1)−y'(t)) for each time t. The computation unit 2040 extracts a plurality of partial periods in which the directions of the computed plurality of velocity vectors are substantially the same from the measurement period of y(t). Note that, y(t+1) is the detected value obtained next to y(t) in the sensor.

The computation unit 2040 computes the direction of the velocity vector of (y(t), y'(t)) in each extracted partial period as the velocity constant corresponding to the partial period. For example, the computation unit 2040 computes a statistical value (average value or the like) of the direction of the velocity vector in each partial period as the velocity constant corresponding to the partial period. In addition, for example, the computation unit 2040 may perform linear regression on a point (y(t), y'(t)) included in the partial period for each partial period and may use the slope of the regression line obtained for each partial period as the velocity constant corresponding to the partial period. Note that, the division of the measurement period of y(t) can be implemented by clustering the velocity vectors based on that direction. Note that, the direction of the velocity vector (y(t+1)−y(t), y'(t+1)−y'(t)) is represented as {y'(t+1)−y'(t)}/{y (t+1)−y(t)}.

Figure 9:
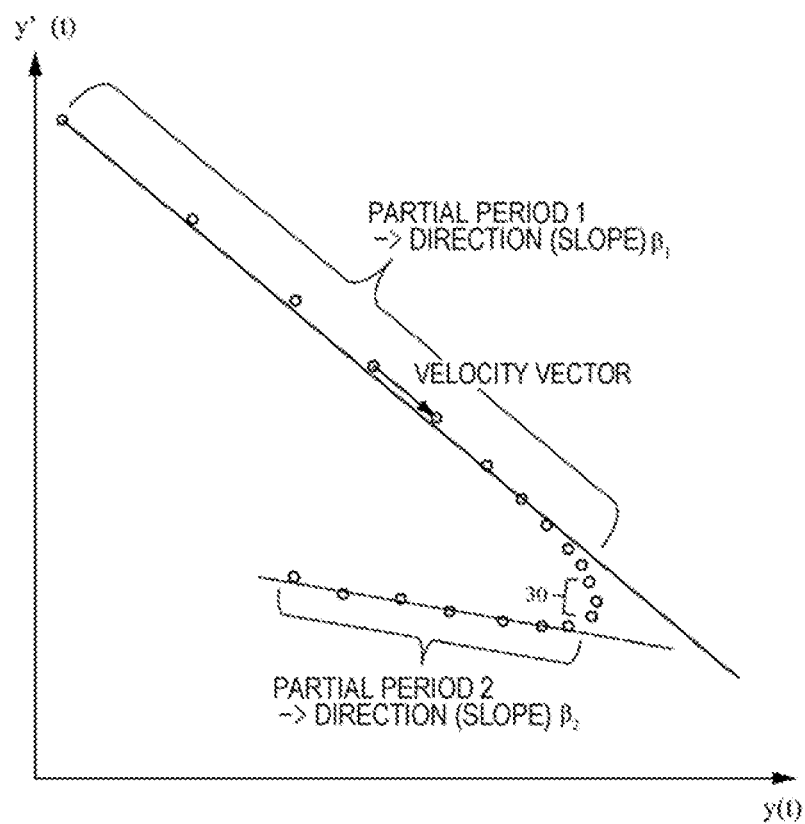
FIG. 9 is a diagram illustrating a velocity vector of (y(t), y'(t)).

FIG. 9 is a diagram illustrating the velocity vector of (y(t), y'(t)). In FIG. 9, two partial periods are obtained from the time-series data 14. The computation unit 2040 computes the velocity constant $\beta_i$ based on the direction of the velocity vector in the partial period 1 and computes the velocity constant $\beta_2$ based on the direction of the velocity vector in the partial period 2.

As in the section 30 illustrated in FIG. 9, in a portion where the direction of the velocity vector changes, a direction different from any of the directions before and after the change may appear for a short period of time. This is the same as the section 20 in FIG. 7. The direction of the velocity vector that appears only for such a short period may not be included in the feature constants. As a specific method, as described in Method 1, a method of determining the minimum value of the length of the partial period or determining the number of feature constants can be used.

<<Computation Method of Contribution Value>>

A method of computing the contribution value corresponding to the feature constant after the feature constant is computed will be described. The computation unit 2040 generates a prediction model for predicting the detected value of the sensor 10 using the set of the contribution values $\xi_i$ (that is, the contribution vector) $\Xi=\{\xi_1, \ldots, \xi_m\}$ corresponding to the set of the computed feature constants $\Theta=\{\theta_1, \ldots, \theta_m\}$, as the parameter. When generating the prediction model, the contribution vector $\Xi$ can be computed by performing a parameter estimation for the contribution vector $\Xi$ by using the time-series data 14 which is the observation data. An example of the prediction model when the velocity constant $\beta$ is used as the feature constant can be represented by Expression (6). Further, an example of the prediction model when the time constant $\tau$ is used as the feature constant can be represented by Expression (7). Various methods can be used for estimating the parameters of the prediction model.

Hereinafter, some examples of the method will be given. Note that, in the following description, a case where the velocity constant $\beta$ is used as the feature constant is described. The method of parameter estimation when the time constant $\tau$ is used as the feature constant can be implemented by reading the velocity constant $\beta$ in the following description as $1/\tau$.

<<Parameter Estimation Method 1>>

For example, the computation unit 2040 estimates the parameter $\Xi$ by a maximum likelihood estimation using the predicted value obtained from the prediction model and the observed value (that is, time-series data 14) obtained from the sensor 10. For the maximum likelihood estimation, for example, the least squares method can be used. In this case, specifically, the parameter $\Xi$ is determined according to the following objective function.

$$\operatorname*{argmin}_{\Xi \in \mathbb{R}^m} \sum_{i=0}^{T-1} |y(t_i) - \hat{y}(t_i)|^2 \qquad (10)$$

T represents the length (the number of detected values) of the time-series data 14. Further, y^(ti) represents the predicted value at time ti.

The vector $\Xi$ that minimizes the above objective function can be computed using the following Expression (11).

$$\Xi = (\Phi^T \Phi)^{-1} \Phi Y \qquad (11)$$

$$\Phi_{k,i} = \begin{cases} 1 - e^{-\beta_k t_i} & \text{when rising} \\ e^{-\beta_k t_i} & \text{when falling} \end{cases}$$

The vector is expressed as Y=(y(t0), y(t1), . . . ).

Therefore, the computation unit 2040 computes the parameter $\Xi$ by applying the time-series data Y and the set of the feature constants $\Theta=\{\beta_1, \beta_2, \ldots\}$ to the above Expression <<Parameter Estimation Method 2>>

For the least squares method described above, a regularization term may be introduced to perform regularization. For example, the following Expression (12) shows an example of performing L2 regularization.

$$\operatorname*{argmin}_{\Xi\in\mathbb{R}^m} \sum_{i=0}^{T-1} |y(t_i) - \hat{y}(t_i)|^2 + \lambda \sum_k \xi_k^2 \qquad (12)$$

$\lambda$ is a hyperparameter representing the weight given to the regularization term.

In this case, the parameter $\Xi$ can be determined according to the following expression (13).

$$\Theta = (\Phi^T\Phi + \lambda I)^{-1}\Phi Y \qquad (13)$$

By introducing such a regularization term, it is possible to suppress the amplification of the measurement error in the matrix computation as compared with the case where the regularization term is not introduced, thereby each contribution value $\xi_i$ can be computed more accurately. Further, by suppressing the amplification of the error, the contribution value is numerically stable, so that the robustness of the feature value with respect to the mixing ratio is improved.

Note that, as described above, $\lambda$, is the hyperparameter and needs to be determined in advance. For example, the value of $\lambda$, is determined through a test measurement and a simulation. It is preferable to set the value of $\lambda$, to a small value so that the contribution value does not oscillate.

The simulation for determining the value of $\lambda$, will be described. In the simulation, in a case where "a single molecule with a contribution of 1" is virtually measured (for example, in the case of falling, when the velocity constant of the single molecule is defined as $\beta_0$, it is expressed as $y(t)=\exp\{-\beta_0*T\}$) is considered, and the result of the feature value estimation value by Expression (13) in this case is observed. Virtually, when it is assumed that the ideal observation (measurement can be performed for an infinitely long time at an infinitesimal measurement interval and the observation error is zero) is possible, in the simulation of a virtual single molecule, the feature value in which only $\beta 0$ has a sharp peak as shown below, is obtained, thereby the original velocity constant $\beta=\beta 0$ and the contribution $\xi=1$ are completely reproduced.

$$\xi_k = \begin{cases} 1, & \beta_k = \beta_0 \\ 0, & \text{otherwise.} \end{cases} \qquad (14)$$

However, since the ideal observation is not possible in reality, the peak of the contribution value becomes blunted or the contribution value oscillates. FIG. 7 is a diagram illustrating the feature value obtained for a single molecule. From this diagram, the trade-off between the peak blunting and the increase of the oscillation can be seen depending on the value of $\lambda$. Specifically, when $\lambda$ is too large, the oscillation decreases, but the peak width increases. When the peak width becomes large, the result of measuring two molecules having similar velocity constants looks like one large peak, and it becomes difficult to distinguish these molecules. That is, the sensitivity is reduced. On the other hand, when $\lambda$ is too small, the peak width decreases, but the oscillation increases. As the oscillation increases, the robustness of the feature value lowers, as will be described later. Therefore, it can be said that it is preferable to sharpen the peak (improve the sensitivity) by determining to reduce $\lambda$ to the extent that the oscillation does not occur (robustness is not impaired).

The purpose of the simulation is to evaluate the degree of occurrence of such peak blunting or the oscillation while changing $\lambda$. In order to quantitatively measure the "oscillation magnitude" and "peak width", for example, the contribution vectors $\Xi_1$ and $\Xi_2$ of two virtual single molecules having two different velocity constants $\beta_1$ and $\beta_2$, respectively, are computed by simulation. Thereafter, the inner product of these two contribution vectors is computed as follows.

$$f(\Delta v) = \langle \Xi_1, \Xi_2 \rangle = \sum_{k=1}^{K} (\Xi_1)_k (\Xi_2)_k \qquad (15)$$

wherein $\Delta v = \log \dfrac{\beta_1}{\beta_2}$

The function $f(\Delta v)$ attenuates while oscillating. Therefore, it can be quantified with the width of the main lobe of the oscillation as the "peak width" and with the level of the side lobes as the "oscillation magnitude". $\lambda$ is determined by selecting a value of $\lambda$ such that the main lobe width is as narrow as possible and the side lobe level is as small as possible.

One of the advantages of suppressing the oscillation of the contribution value is that, as described above, the feature value becomes robust against changes in the time constant and the velocity constant. In other words, the feature value becomes robust with respect to the change in the temperature. The reason will be described below.

When the changes in time constant or the velocity constant occur due to the change in the temperature, the contribution value illustrated in FIG. 7 or FIG. 8 described later move in parallel in the X-axis direction. When the contribution value oscillates greatly, even when the contribution value moves slightly in parallel in the X-axis direction, a distance between the contribution vectors before and after the parallel movement becomes long. That is, even when the time constant or the velocity constant changes slightly, the feature value changes greatly, and the robustness of the feature value with respect to the change in the time constant or the change in the velocity constant becomes low.

In contrast to this, when the oscillation of the contribution value is small, the distance between the contribution vectors before and after the parallel movement becomes short. This means that when the time constant or velocity constant changes slightly, the feature value also changes slightly. That is, it means that the feature value is highly robust. Therefore, it can be said that the robustness of the feature value is improved by suppressing the oscillation of the feature value.

Note that, the regularization in the least squares method is not limited to the L2 regularization described above, and other regularizations such as the L1 regularization may be introduced.

<<Parameter Estimation Method 3>>

In this method, the prior distribution P(s) is set for the parameter E. Thereafter, the computation unit 2040 determines the parameter $\Xi$ by using a Maximum a Posteriori (MAP) estimation that uses the time-series data 14 which is the observed value. Specifically, the parameter $\Xi$ that maximizes the following objective function is adopted.

$$\operatorname*{argmax}_{\Xi} P(Y|\Xi)P(\Xi) \qquad (16)$$

$P(Y|\Xi)$ and $P(\Xi)$ are defined by a multivariate normal distribution, for example, as follows.

$$P(Y|\Xi)=N(Y|\hat{Y},\sigma^2 I)$$

$$P(\Xi)=N(\Xi|0,\Lambda) \qquad (17)$$

$N(\cdot|\mu, \Sigma)$ is a multivariate normal distribution with average $\mu$ and covariance $\Sigma$. Further, the vector is expressed as $\hat{y} = (\hat{y}(t1), \hat{y}(t2), \ldots) = \Phi\Xi$. $\sigma^{\wedge 2}$ is a parameter that represents the variance of the observation error.

$\Lambda$ is a covariance matrix of the prior distribution of $\Xi$, and any semi-normal definite matrix may be given in advance or may be determined by a method described later or the like.

Further, $P(Y|\Xi)$ and $P(\Xi)$ may be determined by a Gaussian process (GP) as follows.

$$P(\xi(\beta)) = GP(\xi(\beta)|0, \Lambda(\beta, \beta'))$$

$$P(y(t)) = N(y(t)|\hat{y}(t), \sigma^2) \quad (18)$$

GP $(\xi(\beta)|\mu(\beta), \Lambda(\beta, \beta'))$ is a Gaussian process having an average value function of $\mu(\beta)$ and a covariance function (kernel function) of $\Lambda(\beta, \beta')$. Further, since the Gaussian process is a stochastic process that generates a continuous function, here, $\xi(\beta)$ is a continuous function that represents the contribution ratio with respect to $\beta$(or $\tau$), and the vector $\Xi$ is a vector $\Xi = (\xi\beta 1), (\beta 2), \ldots)$ in which the values in "$\beta = \beta 1, \beta 2, \ldots$" of the function $\Lambda(\beta)$ are arranged. In this case, Expression (17) can be regarded as a special case of Expression (18), and the (i, j) component of the covariance matrix $\Lambda$ in Expression (17) is a value in $(\beta, \beta') = (\beta_1, \beta_2)$ of the covariance function $\Lambda(\beta, \beta')$ in Expression (18). That is, the matrix $\Lambda$ in Expression. (17) is a Gram matrix in the so-called Gaussian process.

Further, the computation unit 2040 may determine the parameter $\Xi$ by using a Bayesian estimation that uses the time-series data 14 which is the observed value. Specifically, the parameter $\Xi$ is determined by computing the following conditional expected value.

$$\Xi = \mathbb{E}[\Xi|Y] = \frac{\int \Xi P(Y|\Xi) P(\Xi) d\Xi}{\int P(Y|\Xi) P(\Xi) d\Xi} \quad (19)$$

$\Xi[\Xi|Y]$ is a conditional expected value assuming that $\Xi$ and Y follow the probability distribution in Expression (18).

The feature vector $\Xi$ that maximizes the above objective function (14) and the feature vector $\Xi$ obtained by the conditional expected value (19) can both be computed by the following Expression (20).

$$\Xi = \Lambda \Phi^T (\Phi \Lambda \Phi^T + \sigma^2 I)^{-1} Y \quad (20)$$

<<<How to Determine Hyperparameters>>>

When using the Gaussian process, as the hyperparameters that are set in advance, there are a) the form of the covariance function $\Lambda(\beta, \beta')$, b) the parameters of the covariance function, and c) the measurement error parameter $\sigma^{\wedge}2$. The following steps are performed while changing these parameters.

1. Simulate a measurement value of a single molecule with a virtual velocity constant $\beta 0$.
2. Estimate a contribution value from the simulated measurement value.
3. Quantify the magnitude of the oscillation and the peak width of the estimated contribution value.
4. Repeat steps 1 to 3 while changing the hyperparameters a to c above.
5. Determine the hyperparameters a to c such that the oscillation is small and the peak width is narrow by the grid search or the steepest descent method.

Note that, for example, the in-lobe width and side-lobe level of the above-mentioned function $f(\Delta v)$ are used as indexes for quantifying the magnitude of the oscillation and peak width of the feature value. Further, besides that, the variance value (the square variance or absolute value variance) when the estimated $\Xi$ is regarded as a probability distribution may be used. These variance values become smaller values as the oscillation is smaller and the peak width is narrower. Note that, the actual measurement (test measurement) may be carried out instead of the simulation.

<A Case where the Contribution Value is Computed Together with the Feature Constant>

As described above, there is a method of using the least squares method as one of the methods for computing the contribution value corresponding to the feature constant. Instead of using the least squares method after computing the feature constant, the computation unit 2040 may compute both the set $\Theta$ of the feature constants and the set $\Xi$ of the contribution values by solving the combinatorial optimization problem of minimizing the minimum value of the objective function of the least squares method with respect to the set $\Theta$ of the feature constants. Specifically, $\Theta$ that minimizes the following objective function $h(\Theta)$ and the parameter $\Xi$ in the minimized $h(\Theta)$ are the computed results of the computation unit 2040.

$$\operatorname*{argmin}_{\Theta \in \mathbb{R}^m} h(\Theta) \quad (21)$$

$$h(\Theta) = -\min_{\Xi \in \mathbb{R}^m} \sum_{i=0}^{T-1} |y(T_i) - \hat{y}(t_i)|^2 \quad (22)$$

An existing method can be used as a specific method for solving the above-mentioned combinatorial optimization problem. In particular, when all the elements of $\Xi$ are positive numbers, the above objective function becomes a monotonically decreasing submodular function, so that it can be computed accurately by, for example, a greedy algorithm.

<Method of Determining the Number of Feature Constants>

The computation unit 2040 may determine the number of feature constants. The determined number of feature constants can be used, for example, to determine the number of partial periods to be extracted from the domain of g(t) or the measurement period of y(t) described above.

For example, the number of feature constants can be determined by using information criteria such as Akaike's Information Criterion (AIC) and Bayesian Information Criterion (BIC). The function $h(\Theta)$ of Expression (22) described above is used to compute the information criterion. For example, the AIC can be computed as follows. Note that, the method for deriving the following AIC will be described later.

$$L(K) = \min_{|\Theta|=K} h(\Theta) \quad (23)$$

$$AIC = \frac{1}{\sigma^2} L(K) + 4K + T\log(2\pi\sigma^2) \quad (24)$$

Here, $\sigma^{\wedge}2$ is a variance of the observation error.

The computation unit 2040 determines the integer K where the AIC is minimized as the number of feature constants. FIG. 8 is a diagram representing AIC with a graph. In FIG. 8, the upper part is a graph of the function L, and the lower part is a graph of AIC. The integer K where the AIC is minimized is K*. Therefore, the computation unit 2040 sets the number of feature constants to K*.

By determining the number of feature constants using the information criterion in this way, the number of feature constants can be appropriately determined in consideration of a balance between the merit of improving the prediction accuracy obtained by increasing the number of parameters of the prediction model (here, the number of feature constants or the number of contribution values) and the demerit of increasing the complexity of the model by increasing the number of parameters.

The method of deriving the AIC of Expression (24) will be described. First, the definition of the AIC is as follows.

$$AIC = -2 \log l + 2p \qquad (25)$$

Where 1 is the maximum likelihood and p is the number of parameters.

Since the number of feature constants and the number of contribution values are K, respectively, the number of parameters p is 2K. Further, the maximum likelihood is computed as follows.

$$\ell = \max_{\Xi,\Theta} P(Y|\Xi) = \frac{1}{(2\pi\sigma^2)^{\frac{T}{2}}} \exp\left\{-\frac{1}{2\sigma^2} L(K)\right\} \qquad (26)$$

Expression (24) can be obtained by substituting the above 1 and p into the definition of the AIC.

<Output of Feature Value: S106>

The output unit 2060 outputs information (hereinafter, output information) in which the set $\Theta$ of the feature constants and the set $\Xi$ of the contribution values, which are obtained by using the above method, are associated with each other as the feature value representing the feature of the gas (S106). For example, the output information is text data representing the feature matrix F. In addition, for example, the output information may be information that graphically represents the association between the set $\Theta$ of the feature constants and the set $\Xi$ of the contribution values with a table, graph, or the like.

Figure 10:
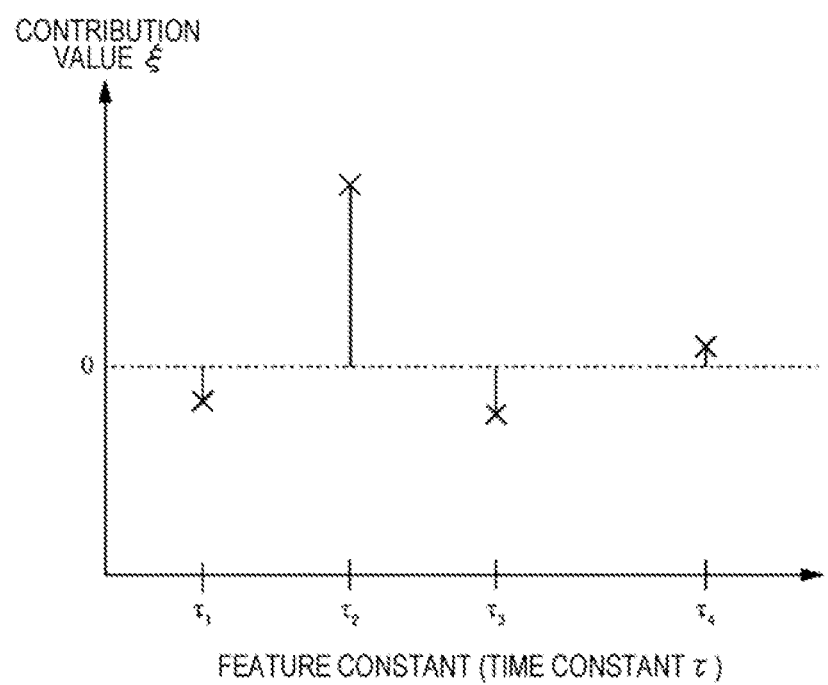
FIG. 10 is a graph illustrating a feature value of a target gas.

FIG. 10 is a graph illustrating the feature value of the target gas. In the graph of FIG. 10, the time constant $\tau$ is shown on the horizontal axis, and the contribution value is shown on the vertical axis. The pairs of $(\tau_i, \xi_i)$ computed by the computation unit 2040 are plotted on the graph. By representing the feature value of the target gas with the graphical information in this way, it becomes easier for a person to intuitively understand the feature of the gas.

There are various specific methods for outputting the output information. For example, the output unit 2060 stores the output information in any storage device. In addition, for example, the output unit 2060 causes the display device to display the output information. In addition, for example, the output unit 2060 may transmit the output information to an apparatus other than the information processing apparatus 2000.

<A Case where a Plurality of Computations are Performed to Associate a Set of Feature Constants with a Set of Contribution Values>

The information processing apparatus 2000 may compute the association between the set $\Theta$ of the feature constants and the set $\Xi$ of the contribution values for each of the plurality of time-series data 14 obtained for the same target gas. In this case, the output unit 2060 may use a set of these plurality of associations as the feature value of the target gas.

For example, the information processing apparatus 2000 computes the set $\Theta_u$ of the feature constants and a set $\Xi_u$ of the contribution values for the rising time-series data 14 and generates a feature matrix $F_u$ in which these sets are associated with each other. Further, the information processing apparatus 2000 computes the set $\Theta_d$ of the feature constants and a set $\Xi_d$ of the contribution values for the falling time-series data 14 and generates a feature matrix $F_d$ in which these sets are associated with each other. The information processing apparatus 2000 outputs $\{F_u, F_d\}$, which is a group of the generated feature matrices, as the feature value of the target gas.

Figure 11:
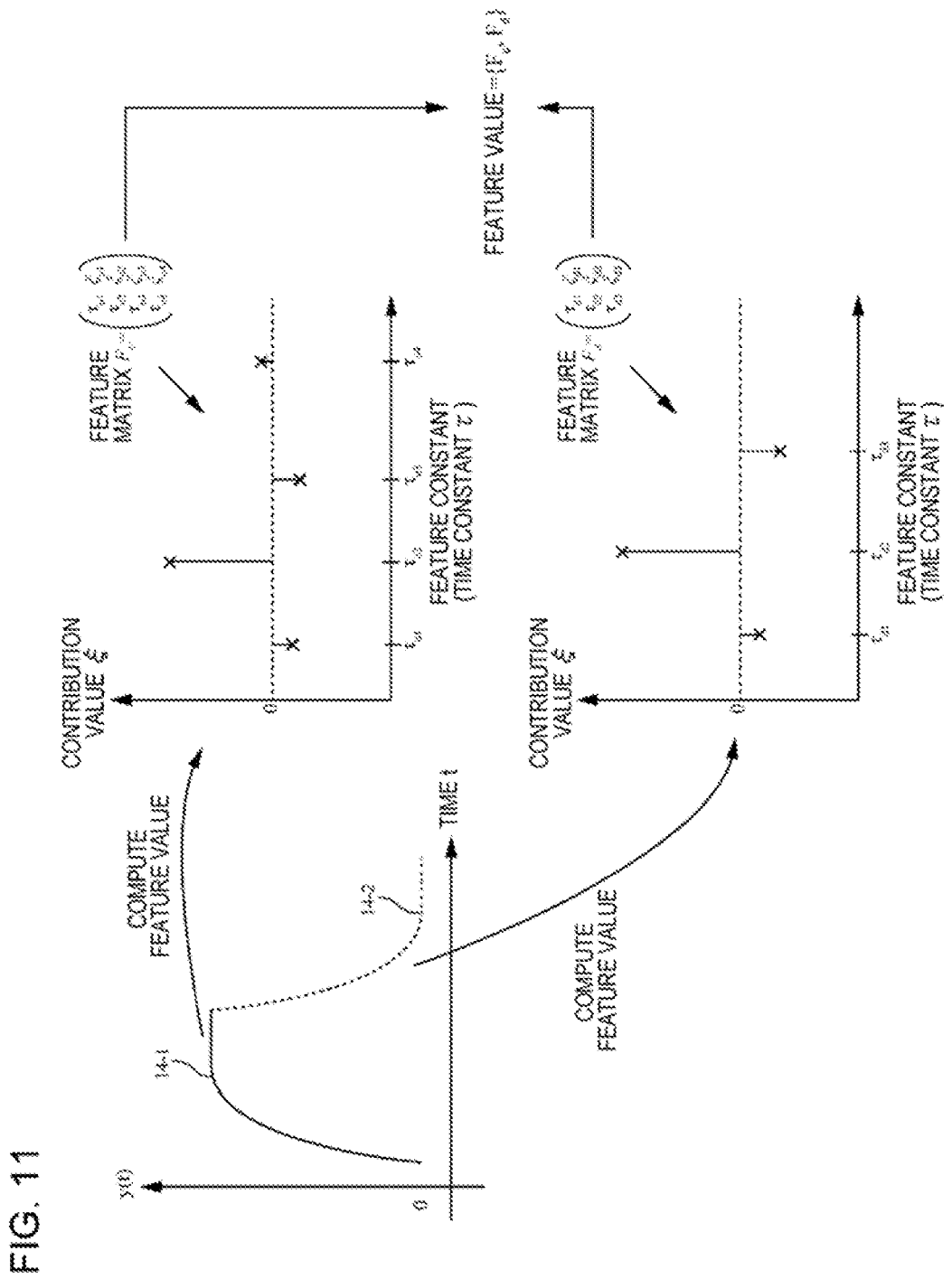
FIG. 11 is a diagram illustrating a case where a feature matrix is obtained from each of rising time-series data and falling time-series data.

FIG. 11 is a diagram illustrating a case where a feature matrix is obtained from each of rising time-series data 14 and falling time-series data 14. In FIG. 11, the feature matrix $F_u$ is obtained from the time-series data 14-1 which is the rising time-series data. Further, the feature matrix $F_d$ is obtained from the time-series data 14-2 which is the falling time-series data. The output unit 2060 outputs $\{F_u, F_d\}$, which is a combination of the two obtained feature matrices, as the feature value of the target gas.

Note that, the output unit 2060 may use one matrix obtained by connecting the feature matrix obtained from the rising time-series data 14 and the feature matrix obtained from the falling time-series data 14 as the feature value of the target gas. For example, in this case, the output unit 2060 outputs $F_c = (\Theta_u T, \Xi_u T, \Theta_d T, \theta_d T)$, in which $F_u = (\Theta_u T, \Xi_u T)$ and $F_d = (\Theta_d T, \Xi_d T)$ are connected to each other, as the feature value of the target gas. Note that, when the number of rows of the feature matrix to be connected is different from each other, by expanding the matrix with the smaller number of rows by a method such as zero padding, the number of rows of the feature matrix to be connected is matched with each other.

The plurality of feature matrices are not limited to those obtained from each of the rising time-series data 14 and the falling time-series data 14. For example, the plurality of time-series data 14 may be obtained by exposing each of the plurality of sensors 10 having different characteristics to the target gas. When the molecules are attached to the sensor, the ease of attachment of each molecule with respect to the sensor differs depends on the characteristics of the sensor. For example, when using a type of sensor in which molecules are attached to the functional membrane, the ease of attachment of each molecule with respect to the functional membrane differs depending on the material of the functional membrane. The same applies to the ease of detachment of each molecule. Therefore, by preparing sensors 10, which have functional membranes made of different materials, and obtaining and analyzing the time-series data 14 from each of the plurality of sensors 10, the features of the target gas can be recognized more accurately.

The information processing apparatus 2000 acquires the time-series data 14 from each of the plurality of sensors 10 having different characteristics and generates the information in which the set of the feature constants and the set of the contribution values are associated with each other for each time-series data 14. The output unit 2060 outputs the group of the plurality of information obtained in this way as the feature value of the target gas.

Figure 12:
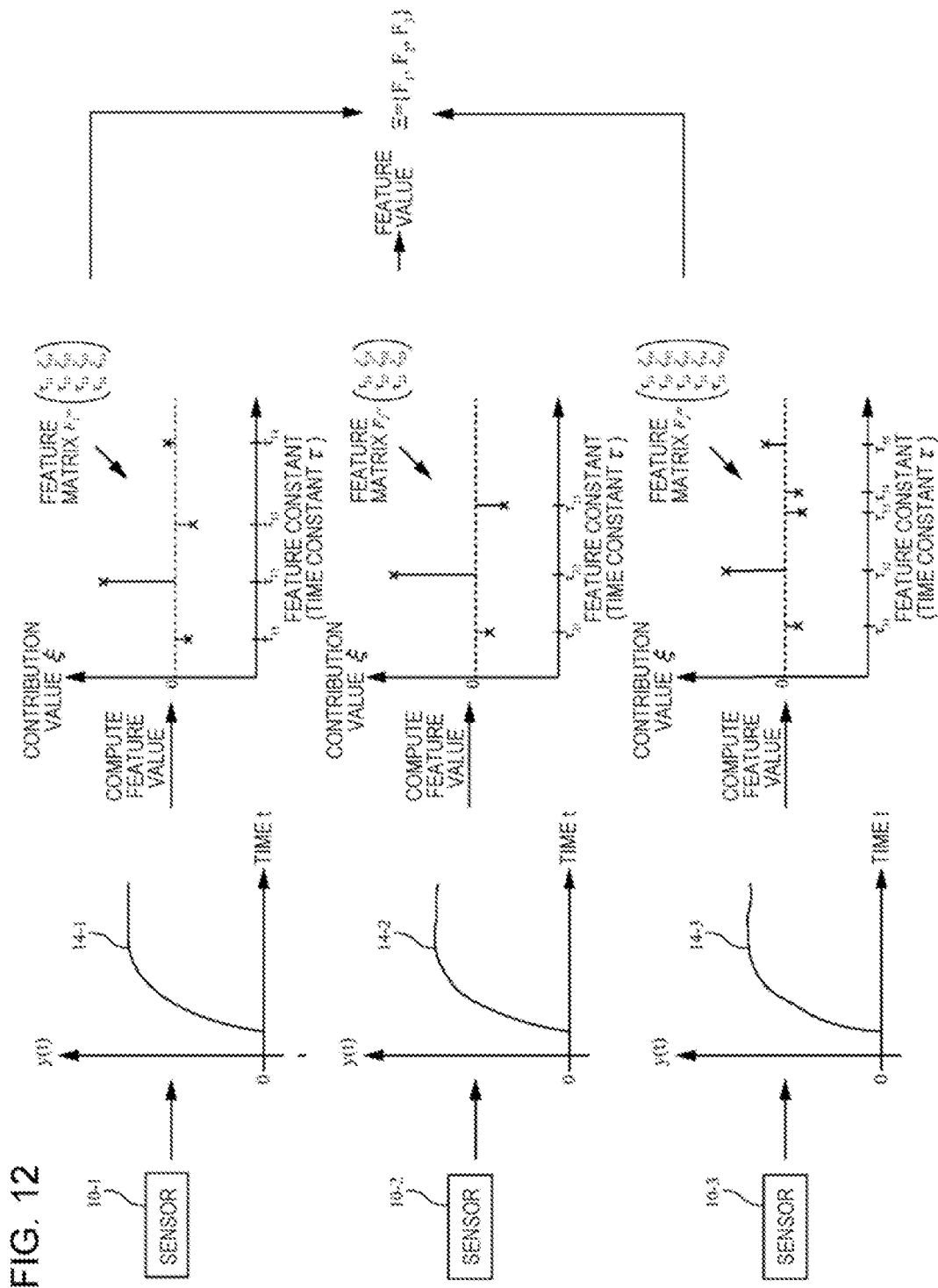
FIG. 12 is a diagram illustrating a case where a plurality of feature matrices are obtained by obtaining the time-series data from each of a plurality of sensors.

FIG. 12 is a diagram illustrating a case where a plurality of feature matrices are obtained by obtaining the time-series data 14 from each of a plurality of sensors 10. In this example, three sensors 10-1, 10-2, and 10-3, each having different characteristics, are prepared, and time-series data

14-1, 14-2, and 14-3 are obtained from each of the three sensors. The information processing apparatus 2000 computes the feature matrices $F_1$, $F_2$, and $F_3$ from each of the plurality of time-series data 14. Thereafter, the information processing apparatus 2000 outputs the group of these three feature matrices as the feature value of the target gas. Note that, as described above, instead of outputting the group of the plurality of feature matrices, one feature matrix $F_c$ in which the plurality of feature matrices are concatenated may be output.

The plurality of sensors 10 having different characteristics may be accommodated in one housing or may be accommodated in different housings. In the former case, for example, the sensor 10 is configured such that a plurality of functional membranes made of different materials are accommodated in one sensor housing and a detected value can be obtained for each functional membrane.

Further, the method described in FIG. 11 and the method described in FIG. 12 may be combined. That is, the information processing apparatus 2000 may obtain the rising time-series data 14 and the falling time-series data 14 from each of the plurality of sensors 10, compute the feature matrix F for each of the obtained time-series data 14, and use the group of the plurality of computed feature matrices or one feature matrix in which the plurality of computed feature matrices are connected, as the feature value of the target gas.

<Computation of Feature Value Considering Bias>

The detected value of the sensor 10 may include a bias term that does not represent a change with time. In this case, the time-series data 14 is represented as follows. Note that, the velocity constant β is used as the feature constant.

$$y(t) = \begin{cases} b - \sum_{k=1}^{K} \xi_k e^{-\beta_k t} & \text{when rising} \\ b + \sum_{k=1}^{K} \xi_k e^{-\beta_k t} & \text{when falling} \end{cases} \quad (27)$$

wherein, b is a bias term defined as follows $$b = \begin{cases} b_0 + \xi_0 & \text{when rising} \\ b_0 & \text{when falling} \end{cases}$$

The Bias is generated, for example, due to the shifting of the offset of the sensor 10. In addition, for example, the bias is generated due to the contribution of components commonly contained in the target gas and the purge gas (for example, the contribution of nitrogen or oxygen in the atmosphere).

The information processing apparatus 2000 may have a function of removing an offset from the time-series data 14. By doing so, the feature value of the target gas can be computed more accurately. Hereinafter, a method of computing the feature value in consideration of the offset will be described.

The computation unit 2040 computes the contribution vector Ξ in consideration of the bias by generating the prediction model of the time-series data 14 represented by the above Expression (27). That is, the computation unit 2040 estimates the parameters Ξ and b for the prediction model represented by the Expression (27). Specifically, the computation unit 2040 estimates Ξ and b by optimizing the objective functions (10), (12), or (16) not only for Ξ but also for b. Note that, when the time constant is used as the feature constant, $\beta_k$ is replaced with $1/\tau_k$ in Expression (27).

For example, it is assumed that Expression (14) is used as the objective function. In this case, the computation unit 2040 computes Ξ and b by the following optimization problem. The same applies when (8) or (10) is used as the objective function.

$$\underset{\Xi, b}{\mathrm{argmax}} P(Y|\Xi, b) P(\Xi, b) \quad (28)$$

The solutions Ξ and b of the above optimization problem can be computed by the following expressions.

$$b = \frac{1^T (\Phi \Lambda \Phi^T + \sigma^2 I)^{-1} Y}{1^T (\Phi \Lambda \Phi^T + \sigma^2 I)^{-1} 1} \quad (29)$$

$$\Xi = \Lambda \Phi^T (\Phi \Lambda \Phi^T + \sigma^2 I)^{-1} (Y - 1b)$$

wherein, vector 1 in which all components are 1.

By estimating both the bias b and the contribution vector Ξ in this way, the effect of the bias is removed from the contribution vector, and the contribution vector can be computed accurately even when the bias is included in the detected value of the sensor 10.

Note that, the output unit 2060 may output the bias b or b0 in addition to the feature matrix F. When the bias is generated due to the shifting of the offset of the sensor, the value of b0 can be used to calibrate the sensor offset.

Although the example embodiments of the present invention have been described above with reference to the drawings, these are examples of the present invention, and various configurations other than the above can be adopted.

The whole or part of the example embodiments disclosed above can be described as, but not limited to, the following supplementary notes.

1. An information processing apparatus including: a time-series data acquisition unit that acquires time-series data of detected values output from a sensor where a detected value thereof changes according to attachment and detachment of a molecule contained in a target gas; a computation unit that computes a plurality of feature constants contributing with respect to the time-series data and a contribution value representing a magnitude of contribution for each feature constant with respect to the time-series data; and an output unit that outputs a combination of the plurality of feature constants and the contribution values computed for each feature constant as a feature value of gas sensed by the sensor, in which the feature constant is a time constant or a velocity constant related to a magnitude of a temporal change of the number of molecules attached to the sensor.

2. The information processing apparatus according to 1., in which the computation unit extracts a plurality of partial periods from a measurement period of the time-series data, and computes the feature constant for each of the partial periods based on a logarithm of a temporal change rate of the detected values in the partial period, and the partial period is a period in which the logarithms of the temporal change rate of the detected values contained in the partial period are substantially the same.

3. The information processing apparatus according to 1., in which the computation unit computes time-series vector data having the detected value at each time and a temporal change rate of the detected values at the time as elements, by using the time-series data, computes a velocity vector for each of the computed time-series vector data, extracts a plurality of partial periods from a measurement period of the time-series data based on a direction of the velocity vector, and computes the feature constant for each of the partial periods based on the direction of the velocity vector in the partial period, and the partial period is a period in which the directions of the velocity vectors contained in the partial period are substantially the same.

4. The information processing apparatus according to any one of 1. to 3., in which the computation unit computes each contribution value by performing, for a prediction model of the detected value of the sensor with the contribution value of each of the plurality of feature constants as a parameter, a parameter estimation that uses the acquired time-series data.

5. The information processing apparatus according to 4., in which the computation unit computes each of the contribution values by performing, for time-series data obtained from the prediction model and the acquired time-series data, a maximum likelihood estimation that uses a least squares method.

6. The information processing apparatus according to 5., in which in the maximum likelihood estimation in the least squares method, a regularization term is included in an objective function.

7. The information processing apparatus according to 4., in which the computation unit computes each of the contribution values by using a Maximum a Posteriori (MAP) estimation or a Bayesian estimation that uses a prior distribution of each of the contribution values and the acquired time-series data.

8. The information processing apparatus according to 7., in which the prior distribution is a multivariate normal distribution or a Gaussian process.

9. The information processing apparatus according to 4., in which the computation unit computes a plurality of feature constants and a plurality of contribution values by minimizing a minimum value of an objective function with respect to the plurality of feature constants for the objective function that represents a square error between the time-series data obtained from the prediction model and the acquired time-series data.

10. The information processing apparatus according to any one of 4. to 9., in which the prediction model contains a parameter that represents a bias, and the computation unit estimates parameters that each represent the contribution value and the bias for the prediction model.

11. The information processing apparatus according to any one of 1. to 10., in which the time-series data acquisition unit acquires a plurality of time-series data, the computation unit computes a group of a set of the feature constants and a set of the contribution values for each of the plurality of time-series data, and the output unit outputs information obtained by combining a plurality of the computed groups of the sets of the feature constants and the sets of the contribution values, as the feature value of the target gas.

12. The information processing apparatus according to 11., in which the plurality of time-series data include both time-series data obtained when the sensor is exposed to the target gas and time-series data obtained when the target gas is removed from the sensor.

13. The information processing apparatus according to 11., in which the plurality of time-series data include time-series data obtained from each of a plurality of the sensors having different characteristics.

14. A control method executed by a computer, the method including: a time-series data acquisition step of acquiring time-series data of detected values output from a sensor where a detected value thereof changes according to attachment and detachment of a molecule contained in a target gas; a computation step of computing a plurality of feature constants contributing with respect to the time-series data and a contribution value representing a magnitude of contribution for each feature constant with respect to the time-series data; and an output step of outputting a combination of the plurality of feature constants and the contribution values computed for each feature constant as a feature value of gas sensed by the sensor, in which the feature constant is a time constant or a velocity constant related to a magnitude of a temporal change of the number of molecules attached to the sensor.

15. The control method according to 14., in which in the computation step, a plurality of partial periods are extracted from a measurement period of the time-series data, and the feature constant is computed for each of the partial periods based on a logarithm of a temporal change rate of the detected values in the partial period, and the partial period is a period in which the logarithms of the temporal change rate of the detected values contained in the partial period are substantially the same.

16. The control method according to 14., in which in the computation step, time-series vector data having the detected value at each time and a temporal change rate of the detected values at the time as elements is computed by using the time-series data, a velocity vector is computed for each of the computed time-series vector data, a plurality of partial periods are extracted from a measurement period of the time-series data based on a direction of the velocity vector, and the feature constant is computed for each of the partial periods based on the direction of the velocity vector in the partial period, and the partial period is a period in which the directions of the velocity vectors contained in the partial period are substantially the same.

17. The control method according to any one of 14. to 16., in which in the computation step, each contribution value is computed by performing, for a prediction model of the detected value of the sensor with the contribution value of each of the plurality of feature constants as a parameter, a parameter estimation that uses the acquired time-series data.

18. The control method according to 17., in which in the computation step, each of the contribution values is computed by performing, for time-series data obtained from the prediction model and the acquired time-series data, a maximum likelihood estimation that uses a least squares method.

19. The control method according to 18., in which in the maximum likelihood estimation in the least squares method, a regularization term is included in an objective function.

20. The control method according to 17., in which in the computation step, each of the contribution values is computed by using a Maximum a Posteriori (MAP) estimation or a Bayesian estimation that uses a prior distribution of each of the contribution values and the acquired time-series data.

21. The control method according to 20., in which the prior distribution is a multivariate normal distribution or a Gaussian process.

22. The control method according to 17., in which in the computation step, a plurality of feature constants and a plurality of contribution values are computed by minimizing a minimum value of an objective function with respect to the plurality of feature constants for the objective function that represents a square error between the time-series data obtained from the prediction model and the acquired time-series data.

23. The control method according to any one of 17. to 22., in which the prediction model contains a parameter that represents a bias, and in the computation step, parameters that each represent the contribution value and the bias are estimated for the prediction model.

24. The control method according to any one of 14. to 23., in which in the time-series data acquisition step, a plurality of time-series data are acquired, in the computation step, a group of a set of the feature constants and a set of the contribution values is computed for each of the plurality of time-series data, and in the output step, information obtained by combining a plurality of the computed groups of the sets of the feature constants and the sets of the contribution values is output as the feature value of the target gas.

25. The control method according to 24., in which the plurality of time-series data include both time-series data obtained when the sensor is exposed to the target gas and time-series data obtained when the target gas is removed from the sensor.

26. The control method according to 24., in which the plurality of time-series data include time-series data obtained from each of a plurality of the sensors having different characteristics.

27. A program that causes a computer to execute each step of the control method according to any one of 14. to 26.

The invention claimed is:

1. An information processing apparatus comprising:
at least one non-transitory memory storing instructions; and
at least one processor configured to execute the instructions to perform operations comprising:
acquiring time-series data of detected values output from a sensor according to attachment and detachment of a molecule contained in a target gas containing a plurality of molecules of different types, wherein the sensor outputs the detected values based on changes in physical quantities of a member of the sensor that occur in response to the attachment and detachment of the molecule with respect to a receptor;
computing a plurality of feature constants regarding the time-series data and a contribution value representing a magnitude of contribution for each feature constant with respect to the time-series data; and
outputting a combination of the plurality of feature constants and the contribution values as a feature value of the target gas sensed by the sensor, wherein
each feature constant is a time constant or a velocity constant related to a magnitude of a temporal change of a number of molecules attached to the sensor, such that a feature the target gas is extracted from the detected values output from the sensor even though the plurality of molecules are of different types,
computing the plurality of feature constants and the contribution value for each feature constant comprises:
computing time-series vector data having, as elements, the detected values at a respectively plurality of times and a temporal change rate of the detected values at the respective plurality of, by using the time-series data;
computing a velocity vector for the computed time-series vector data;
extracting a plurality of partial periods from a measurement period of the time-series data based on a direction of the velocity vector; and
computing the feature constant for each of the partial periods based on the direction of the velocity vector in the partial period, and
the partial period is a period in which the direction of the velocity vector throughout the partial period is substantially the same.

2. The information processing apparatus according to claim 1, wherein
computing the plurality of feature constants and the contribution value for each feature constant comprises computing the contribution value for each feature constant by performing, for a prediction model of a respective detected value of the sensor with the contribution value as a parameter, a parameter estimation that uses the acquired time-series data.

3. The information processing apparatus according to claim 2, wherein
computing the plurality of feature constants and the contribution value for each feature constant comprises computing the contribution value for each feature constant by performing, for time-series data obtained from the prediction model and the acquired time-series data, a maximum likelihood estimation that uses a least squares method.

4. The information processing apparatus according to claim 3, wherein
in the maximum likelihood estimation in the least squares method, a regularization term is included in an objective function.

5. The information processing apparatus according to claim 2, wherein
computing the plurality of feature constants and the contribution value for each feature constant comprises computing the contribution value for each feature constant by using a Maximum a Posteriori (MAP) estimation or a Bayesian estimation that uses a prior distribution of each of the contribution value and the acquired time-series data.

6. The information processing apparatus according to claim 5, wherein
the prior distribution is a multivariate normal distribution or a Gaussian process.

7. The information processing apparatus according to claim 2, wherein
computing the plurality of feature constants and the contribution value for each feature constant comprises minimizing a minimum value of an objective function with respect to the plurality of feature constants for the objective function that represents a square error between the time-series data obtained from the prediction model and the acquired time-series data.

8. The information processing apparatus according to claim 2, wherein
the prediction model contains a parameter that represents a bias, and
computing the plurality of feature constants and the contribution value for each feature constant comprises estimating parameters that each represent the contribution value and the bias for the prediction model.

9. The information processing apparatus according to claim 1, wherein
acquiring the time-series data comprises acquiring a plurality of time-series data,
computing the plurality of feature constants and the contribution value for each feature constant comprises computing a group of a set of the feature constants and a set of the contribution values for each of the plurality of time-series data, and
outputting the combination of the plurality of feature constants and the contribution values comprises outputting information obtained by combining the computed group for each of the plurality of time-series data, as the feature value of the target gas.

10. The information processing apparatus according to claim 9, wherein
the plurality of time-series data include both
time-series data obtained when the sensor is exposed to the target gas, and
time-series data obtained when the target gas is removed from the sensor.

11. The information processing apparatus according to claim 9, wherein
the plurality of time-series data include time-series data obtained from each of a plurality of the sensors having different characteristics.

12. The information processing apparatus according to claim 1, wherein the sensor has a functional membrane to which the molecule is attached as the receptor, and stress generated in a supporting member of the functional membrane is changed due to the attachment and detachment of the molecule with respect to the functional membrane.

13. A control method executed by a computer, the method comprising:
acquiring time-series data of detected values output from a sensor according to attachment and detachment of a molecule contained in a target gas containing a plurality of molecules of different types, wherein the sensor outputs the detected values based on changes in physical quantities of a member of the sensor that occur in response to the attachment and detachment of the molecule with respect to a receptor;
computing a plurality of feature constants regarding the time-series data and a contribution value representing a magnitude of contribution for each feature constant with respect to the time-series data; and
outputting a combination of the plurality of feature constants and the contribution values as a feature value of the target gas sensed by the sensor, wherein
each feature constant is a time constant or a velocity constant related to a magnitude of a temporal change of a number of molecules attached to the sensor, such that a feature the target gas is extracted from the detected values output from the sensor even though the plurality of molecules are of different types,
computing the plurality of feature constants and the contribution value for each feature constant comprises:
computing time-series vector data having, as elements, the detected values at a respectively plurality of times and a temporal change rate of the detected values at the respective plurality of, by using the time-series data;
computing a velocity vector for the computed time-series vector data;
extracting a plurality of partial periods from a measurement period of the time-series data based on a direction of the velocity vector; and
computing the feature constant for each of the partial periods based on the direction of the velocity vector in the partial period, and
the partial period is a period in which the direction of the velocity vector throughout the partial period is substantially the same.

14. The control method according to claim 13, wherein the sensor has a functional membrane to which the molecule is attached as the receptor, and stress generated in a supporting member of the functional membrane is changed due to the attachment and detachment of the molecule with respect to the functional membrane.

15. A non-transitory storage medium storing a program that causes a computer to execute a control method, the method comprising:
acquiring time-series data of detected values output from a sensor according to attachment and detachment of a molecule contained in a target gas containing a plurality of molecules of different types, wherein the sensor outputs the detected values based on changes in physical quantities of a member of the sensor that occur in response to the attachment and detachment of the molecule with respect to a receptor;
computing a plurality of feature constants regarding the time-series data and a contribution value representing a magnitude of contribution for each feature constant with respect to the time-series data; and
outputting a combination of the plurality of feature constants and the contribution values as a feature value of the target gas sensed by the sensor, wherein
each feature constant is a time constant or a velocity constant related to a magnitude of a temporal change of a number of molecules attached to the sensor, such that a feature the target gas is extracted from the detected values output from the sensor even though the plurality of molecules are of different types,
computing the plurality of feature constants and the contribution value for each feature constant comprises:
computing time-series vector data having, as elements, the detected values at a respectively plurality of times and a temporal change rate of the detected values at the respective plurality of, by using the time-series data;
computing a velocity vector for the computed time-series vector data;
extracting a plurality of partial periods from a measurement period of the time-series data based on a direction of the velocity vector; and
computing the feature constant for each of the partial periods based on the direction of the velocity vector in the partial period, and
the partial period is a period in which the direction of the velocity vector throughout the partial period is substantially the same.

16. The non-transitory storage medium according to claim 15, wherein the sensor has a functional membrane to which the molecule is attached as the receptor, and stress generated in a supporting member of the functional membrane is changed due to the attachment and detachment of the molecule with respect to the functional membrane.

\* \* \* \* \*